United States Patent [19]

Shanbrom

[11] Patent Number: 5,019,495
[45] Date of Patent: May 28, 1991

[54] TISSUE CULTURE ANTIVIRAL PROCESSES AND COMPOSITIONS

[76] Inventor: Edward Shanbrom, 2252 Liane La., Santa Ana, Calif. 92705

[21] Appl. No.: 433,541

[22] Filed: Nov. 7, 1989

Related U.S. Application Data

[63] Continuation-in-part of Ser. No. 321,522, Mar. 9, 1989, abandoned, Ser. No. 290,161, Dec. 28, 1988, Pat. No. 4,891,221, and Ser. No. 276,113, Nov. 23, 1988, abandoned.

[51] Int. Cl.⁵ ........................... A01N 1/02; C12N 5/00
[52] U.S. Cl. ............................................ 435/1; 435/2; 435/235.1; 435/240.1; 435/240.2
[58] Field of Search .................... 435/240.1, 1, 2, 235, 435/172.1, 240.2

[56] References Cited

PUBLICATIONS

Pompei et al.,-Chem. Abst., vol. 92 (1980), p. 191,170n.
Pompei et al.,-Chem. Abst., vol. 92 (1980), p. 122,494j.
Pompei et al.,-Nature (London), vol. 281, (Oct. 1979), pp. 689-690.
Pompei et al.,-Experientia, vol. 36, No. 3, (1980), p. 304.

*Primary Examiner*—Sam Rosen
*Attorney, Agent, or Firm*—Grant L. Hubbard

[57] ABSTRACT

Nutrient, such as fetal calf serum, for tissue culture medium comprising serum and one or more glycyrrhizic triterpenoid compounds and delipidated albumin to inactivate BVD, CMV and other susceptible viruses and processes of protecting tissue cultures from viral infection are disclosed.

6 Claims, No Drawings

TISSUE CULTURE ANTIVIRAL PROCESSES AND COMPOSITIONS

CROSS-REFERENCE TO RELATED APPLICATION

This is a continuation-in-part of my copending U.S. patent applications Ser. No. 07/321,522, filed Mar. 9, 1989, now abandoned, Ser. No. 07/290,161, filed Dec. 28, 1988, now U.S. Pat. No. 4,891,221, and Ser. No. 07/276,113, filed Nov. 23, 1988, now abandoned, to which priority is claimed.

FIELD OF THE INVENTION

This invention relates to the treatment of tissue cultures and tissue culture media with one or more of a class of compounds referred to here as glycyrrhizic triterpenoid compounds, exemplary of which are glycyrrhizin, glycyrrhizinic acid or glycyrrhetinic acid glycoside, and analogous triterpenes, e.g. carbenoxolone and cicloxolone and their derivatives, to inactivate viruses, such as cytomegalovirus, and bovine diarrhea virus.

BACKGROUND OF THE INVENTION

This invention relates to the preparation, treatment and handling of cultures of tissues and cells. Technically, if a tissue is explanted into the culture media for the purpose of propagating its cells, the procedure is called tissue culture whereas the explanting of individual cells into culture media would be called cell culture; however, both procedures are often referred to by the term "tissue culture" procedures without differentiation, unless the distinction is critical for some ancillary reason.

Tissue cultured cells are extremely fragile in many ways, having exacting requirements not only as to nutrients but also to the amount and type of resident ions which can be tolerated, and culture media are highly susceptible to bacterial and/or viral infection.

It is, generally, impossible to define with precision the exact materials required to propagate a given cell line and, therefore, it is common practice to use media based upon or containing serum and to add nutrient serum as needed during the cell propagation. Bovine serum from adult animals may be suitable in some instances, but fetal bovine serum (FBS) (sometimes referred to as fetal calf serum (FCS) is required for the safe propagation of many cell lines, and where high purity is critical. Even the use of FBS is not, however, a guarantee of freedom from infective agents. Indeed, every lot of commercially produced FBS is contaminated with infectious bovine viral diarrhea (BVD) virus. At best, pools of raw serum probably contain at least $10^4$ infectious BVD virus particles per milliliter.

The most common viral contaminants of fetal bovine serum (FBS) are infectious bovine rhinotracheitis (IBR), parainfluenza 3 (Pl 3) and bovine viral diarrhea (BVD) viruses.

Routine screening of serum for BVD virus contamination is not often successful in detecting the virus because the most common contaminants are noncytopathic, the serum contains antiviral antibody, BVD virus is immunosuppressive so it is difficult to prepare fluorescent antibody conjugates that have high titers to all three BVD virus serotypes, and only a small fraction of the total serum pool can be tested. Therefore, a negative test is always a false negative.

Cells of bovine, porcine, canine, feline, ovine, leporine and simian origin have been found to be sensitive to BVD virus infection. Bovine viral diarrhea virus has been shown to be immunosuppressive to bovine peripheral blood mononuclear cells, and BVD-virus-infected cells are refractory to the antiviral effect of interferon.

FBS is filtered through three double layered, 0.1 um (100 nm) pore size filters to remove animal virus other than BVD virus. Evidently, this procedure virtually eliminates IBR and Pl 3 viruses because they are much larger in size than BVD virus, and their level of contamination in raw pools of FBS is relatively low.

There are, of course, steps that can be followed to reduce BVD viru virus contamination in FBS, but no known procedure, which does not adverely effect the FBS, is totally reliable. In general, those working in the field of tissue culture simply tolerate some BVD virus contamination. The level of BVD virus contamination that is acceptable will depend upon the infectivity of the virus and the susceptibility of the cells that are to be cultured in the presence of the serum. Viruses usually have a very low level of infectivity even for the most sensitive cells. The total particle to infectious particle ratio may be as low as 1, i.e., every virus particle is infectious. The other extreme would be cells that are completely refractory and those that are very resistant to infection. This undoubtedly is the situation with the majority of cells that are cultured in media supplemented with FBS. Generally, the highest level of BVD virus that will ever be encountered in FBS would be $10^5$ infectious BVD virus particles per milliliter. The tissue culture worker must then determine the level of contamination that would be acceptable in the work being undertaken. This level may be one virus per $10^5$ liters for a vaccine manufacturer, or one per $10^2$ liters for an investigator who uses 1 liter of serum per year.

The anti-BVD virus type 3 antibody titer needs to be considered when determining the uses for a given lot of FBS. A higher type 3 antibody titer may give some degree of protection; however, this is insufficient for many purposes, e.g. in the manufacture of vaccines. The worker must then select a serum with a low level of hemoglobin or lactate dehydrogenase (LDH). The rationale being that most of the BVD virus in blood is associated with infected lymphocytes. Lactate dehydrogenase is an indicator of lysis of both leukocytes and erythrocytes. If relatively few blood cells are ruptured, then the number of viruses released into the serum will be reduced. Hemoglobin, which is an indicator of erythrocyte rupture, can be observed visually. If the red cells are lysed during collection and processing of the blood, then many of the white cells are probably also going to be ruptured.

Use of one or more of the serum treatments to further reduce the viral contaminants in the filtered serum. The simplest produre has been to heat inactivate the serum at 56° or 60° C. Sixty degrees celsius may be desirable if the serum is to be used for the cultivation of nonfastidious cells; however, care must be taken to prevent gelling.

Other viruses may also infect tissue cultures. One of the more common infective virus is cytomegalovirus. Cytomegalovirus (CMV) is probably the most ubiquitous of the pathogenic viruses. Virtually all of the people living in the developing countries become infected with CMV early in life, and CMV infects over half the population in the developed countries of the world. CMV may remain essentially inactive in the body following an initial infection and may flare in to an active infection any time, most frequently when the body's immune system is compromised to a greater or lesser degree by disease, radiation or chemotherapy, drug therapy, surgical trauma, etc. CMV is frequently associated with, and may be a causative or contributing factor in, life-threatening disease in individuals with suppressed immune systems, and can be a principal causative factor in pneumonia, neurological disorders, febrile illness, ocular disease and hepatitis. CMV-type viruses also found in virtually all mammals.

Heat, radiation and chemicals used to inactivate viruses in serum all act on viral nucleic acids, proteins, lipids and/or carbohydrates. Similar serum macromolecules and their precursors that serve as nutrients for cells are also damaged by serum treatments. This results in some loss of the serum's capacity to support cell growth. The more extensive the treatment, the greater the damage.

With current technology, a combination of treatments is required to adequately reduce viruses in serum. Several different brief treatments will spread the damage over a relatively large number of serum components, while selected components in a serum treated extensively with a single treatment will be excessively damaged.

All treatments will not inactivate viruses in serum at the same rate. It is desirable, therefore, to determine the inactivation rate for each treatment to be used. Unfortunately, this is not feasible since each serum that is to be treated has its own unique concentration of components that influence the inactivation of viruses.

Serum quality can be damaged by filtration if significant amounts of serum components are adsorbed to the filters or if macromolecules are sheared. Shearing of macromolecules during filtration occurs generally when tangential flow filtration is used and turbulence develops. It is currently very difficult to obtain reliable results on the removal of BVD viruses from serum using filtration.

The BVD virus is a member of the genus Pestivirus of the Togaviridae family. The togaviruses are enveloped and have icosahedral nucleocapsids. The BVD virus is especially pleomorphic; therefore, there may be small infectious forms of the virus that pass more readily through filters than the larger forms.

Users of FBS should assume that every serum is contaminated with the maximum amount of virus that will ever be present in serum and, according to current practice, must decide how to treat the serum to reduce the virus to a level that is acceptable for their work. Currently, this cannot be accomplished with a single treatment. Such treatments include selecting a serum that has had minimal release of virus from leukocytes into the serum and/or that has been filtered through the most virus-retentive filter system that is available, heat inactivation of the virus in the serum, treating the serum with radiation and/or chemicals, determining the susceptibility of the cells to be cultured to BVD virus infection, and selecting the treatment which would, hopefully, reduce BVD virus infection with minimum damage to the serum.

The presence of adventitious viruses in cell cultures is well recognized, and when the cultures are of primate origin there are serious hazards for the production of human viral vaccines. This is one reason for the increasing use of bovine cell cultures. These cultures, however, are not free from viral contamination. Calf kidney (CK) and calf testis (CT) cells were often infected by non-cytopathic mucosal disease virus (MDV): the cells seemed morphologically healthy, but nearly all showed fluorescence with BVD antiserum and rabbit-antibovine conjugate.

BVD is antigenically related to hog cholera virus and morphologically similar to rubella virus. The role of FCS, as a source of contamination by BVD, has been examined by growing CT cells in medium supplemented with either unheated or heated FCS. Heated FCS had been held at 56° C. for 30 min because these conditions inactivated BVD. The incidence of infection of each cell batch grown in unheated FCS was compared with the incidence of infection of the same cell batch grown in heated FCS. Out of fourteen batches of CT cells grown in five batches of FCS, all of the fourteen batches of cells grown in the presence of unheated FCS became infected by BVD. Even when grown in the presence of heated FCS, one of the fourteen batches became infected by the virus.

The other possible source of non-cytopathic BVD, the cells themselves, was examined by fluorescent antibody staining of CK cells which were grown in the presence of heated FCS and subcultured only once. Ten of sixty-three cell batches examined showed BVD fluorescence. Two continuous cell lines were also found to be infected by non-cytopathic BVD.

The conventional interference test, used for screening FCS and bovine cells, relies on detection of a visible inhibition of virus-induced cytopathic effect and probably would not detect the relatively low level of interference. There are, thus, at least two different sources of contamination by non-cytopathic BVD. First, BVD may be found in commercially produced FCS because heat treatment of serum reduces the incidence of infection of CT cells from 100% to 10%. Second, BVD may be indigenous to bovine cells.

In one screening test, wherein five representative commercial batches of FCS were screened for BVD, all batches contained BVD. These results indicate a much higher incidence of contamination than reported previously and illustrate the inadequacy of commercial screening methods.

Infection of bovine cell cultures by non-cytopathic BVD has particular significance for the production of viral vaccines. In one evaluation live infectious bovine rhinotracheitis vaccines from all licensed producers in the United States were tested, and it was found that 8% were contaminated by BVD. Vaccination with such vaccines may give rise to abortions since transplacental infection by BVD can cause death and malformation of the fetus.

The importance of contamination by BVD with regard to human viral vaccines is unknown, but measles virus vaccine and a potential respiratory syncytial virus vaccine are produced on bovine kidney cells grown in the presence of unheated commercial FCS. Contamination of viral stocks also has important implications for experimental virology. For example, in a trial designed to assess the clinical responses of calves to infection by respiratory syncytial (RS) virus, the RS viral inoculum, grown in CK cells, was found to contain BVD. If BVD had not been detected, the clinical reactions of inoculated animals would have been attributed solely to RS virus.

As illustrated by the foregoing discussion, the problem of obtaining BVD-free FCS for research and for commercial vaccine and other biological production is one of great magnitude, and an effective and inexpensive solution to the problem would be of great scientific and economic value.

Economically and in the interest of using limited supplies of FCS it would be of great importance to be able to assure that each FCS nutrient addition to a tissue culture was free of BVD, CMV and other virus which may infect the entire batch, which may be worth tens or hundreds of thousands of dollars, rendering it valueless.

Licorice is a well-known flavoring agent. In addition to its use as a flavoring agent, licorice has long been a common folk medicine for the treatment of sore throats. While not widely known, various extracts of and preparations derived from licorice, e.g. glycyrrhizin and its derivatives, principally the salts of glycyrrhizic acid, have also been used to a limited degree for many years as an orally administered medication for the treatment of peptic ulcers (Chandler, R. F., *Can. Pharm. J.*, V118, No. 9, 1985), and oral administration of glycyrrhizin contemporaneously with saponin antiinflamatory agents has been reported to inhibit saponin and saponigen hemolysis (Segal, R. et al., *Biochem. Pharmacol.* 26, 7 1977).

The family of compounds of interest are, chemically, referred to as triterpenoids. The specific triterpenoids of interest are, principally, derived as extracts or derivatives of glycyrrhiza and are referred to here as GTPD compounds. GTPDs have been evaluated extensively in vitro, and have been administered orally, intramuscularly and intravenously. No significant toxicity from limited, short term administration of glycyrrhizin has been reported. Adverse reactions have been reported in certain instances of prolonged oral ingestion and a slight relapse after rapid discontinuation of intravenous administration of Stronger Neo-Minaphagen C (SNMC) solution, glycyrrhizin (0.2%), cysteine(0.1%) and glycine (2%) was attributed to the steroid ring in glycyrrhizin (Fujisawa K. et al., *Asian Med. J.* (Japan), 23,10 1980). Dosages of SNMC as high as 60 ml/day (~12 mg/dy of glycyrrhizin) have been reported (Iwamura K., *Therapiewoche* (W. Germany) 30,34 1980).

Inactivation of viruses, in vitro, under certain conditions, has been reported (see, e.g., Pompei R., *Exprientia* (Switzerland) 36/3 1980). Such anti-viral activity as GTPD compounds sometimes exhibit has been attributed to reverse transcriptase-inhibitory activity (Nakashima, H. et al., *Jpn. J. Cancer. Res.* 78,8 1987) and to enhancement of interferon-gamma production (Shinada, M. et al., *Proc. Soc. Exp. Biol.* 181,2 1986), but the exact mechanism of the anti-viral function has not been confirmed.

Dargan, D. J., and Subak-Sharpe, J. H., (J. Gen. Virol., 1985-1986) reported antiviral action of carbenoxolone and cicloxolone on herpes simplex virus. Their dose-response experiments showed cicloxolone sodium or carbenoxolone sodium interfered with the HSV replication cycle and reduced the infectious virus yield by 10,000- to 100,000-fold, cicloxolone being the more potent anti-herpes agent, but no consistent effect on HSV DNA synthesis was identified. Some inhibition of cellular DNA synthesis was observed, but this was relatively slight.

Csonka, G. W. and Tyrrell, D. A. (*Br. J. Vener. Dis.* 1984, 60 (3) p178) undertook a double blind clinical study to compare the efficacy of carbenoxolone and cicloxolone creams with placebo in initial and recurrent herpes genitalis and reported significant differences in the time to disappearance of pain and the healing of lesions using cicloxolone, but carbenoxolone showed insignificant beneficial effect.

GTPDs have also been evaluated therapeutically as anti-viral agents in the chemotherapy of acquired immune deficiency syndrome (AIDS) (Ito, M., Yamamoto, N., *Yakaguaku Zasshi* (Japan) 188,2 1988), treatment of Epstein-Barr virus (EBV) infections (Van Benschoten, M. M., *Am. J. Acupunct*, 16,1 1988), and in the treatment of chronic hepatitis (Fujisawa, K. et al., *Asian Med. J.* (Japan), 23,10 1980).

The anti-viral activity of GTPDs varies so unpredictably as to preclude any generalized statements as to whether such compounds have general anti-viral effect or even as to whether such compounds will generally have anti-viral value as to any given virus. While GTPD drugs do, in some environments and under some conditions, exhibit some activity against some viruses, no anti-viral therapy based on GTPDs or in vitro antiviral application of GTPDs has been generally accepted. The AIDS-causing viruses, HIV-I and HIV-II, are the first retroviruses identified as pathogenic in man. While HIV are more fragile than most infectious viruses and are susceptible to destruction by most virus-inactivating methods, such as heating, use of detergent compounds, etc., these methods also damage cells. In addition, any substance added to blood will, unless removed, remain in the medium, and must, therefore, be non-toxic when the medium is used.

The addition of detergents to various blood fractions has been described. My European Patent Specification No. 0 050 061, published Dec. 11, 1985, in which the term "detergent" is equated with the term "amphophil" to encompass cationic, anionic and nonionic detergents, describes the addition of various detergents to plasma protein products and suggests the addition thereof to other blood derivative products to inactivate virus and for other purposes, followed by the removal of the detergent from the product. High concentrations of detergents, from 0.25 to 10%, were required the process described in the European patent specification.

Bosslet and Hilfenhause, European Patent Specification No. 0 278 487, discloses that high concentrations of selected detergents inactivate certain envelope viruses.

Neurath and Horowitz, e.g. U.S. Pat. Nos. 4,540,573, 4,481,189, and 4,591,505, indicate, however, that detergent alone is not effective as an antiviral agent in blood plasma and related products. In spite of these teachings, however, it seems safe to conclude that at least some classes of detergents in high concentrations in some types of blood derivatives do have some inactivating effect. The extent and efficacy of such procedures seems open to considerable doubt, however.

The major constituent of plasma is albumin whose primary role is that of osmotic regulation; it is responsible for 75-80% of the osmotic pressure of plasma. Albumin also serves important roles in the transport of small molecules such as drugs.

An important feature which segregates albumin from other colloids as well as crystalloids is its unique ability to bind reversibly with both anions and cations; hence, albumin can transport a number of substances including fatty acids, hormones, enzymes, dyes, trace metals, and drugs. Substances which are toxic in the unbound or free state are generally not toxic when bound to albumin. This binding property also enables albumin to regulate the extracellular concentration of numerous endogenous as well as exogenously administered substances.

Albumin in general has three types of binding sites (one for acidic, one for basic, and one for neutral compounds), and it plays a critical role in the binding and transport of lipid and lipid-soluble material. Albumin binds with and transports many administered drugs. Because of the phenomenon of mutual displacement of similar type substances, adverse drug interactions may occur. This phenomenon may have important ramifications during disease states such as sepsis, burn injury, and circulatory shock due to a number of etiologies, especially in conjunction with treatment with drugs which may be toxic at high concentrations.

Human serum albumin is believed to be a scavenger of oxygen-free radicals, an important phenomenon which also extends to scavenging of radicals required for lipid peroxidation.

Albumin is a potent scavenger of oxygen radicals. Concentrations of human serum albumin below those present in normal human plasma completely inhibit the inactivation of $\alpha_1$-antiproteinase ($\alpha_1$-proteinase inhibitor [$\alpha_1$-PI], $\alpha_1$-antitrypsin) by hypochlorous acid.

It is known that albumin binds to glycyrrhizic triterpenoids. Carbenoxolone is a potent ulcer-healing drug which is extensively bound to plasma proteins and therefore has the potential for displacement interaction. Carbenoxolone has been shown to be bound to human serum albumin in vitro at a different class of binding site to many other drugs and does not potentiate the pharmacological activity of warfarin, tolbutamide, chlorpropamide or phenytoin in the rat. Thornton PC; Papouchado M; Reed PI *Scand J Gastroenterol Suppl* 1980, 65 p35–9

The binding of glycyrrhizin to human serum and human serum albumin (HSA) was examined by an ultrafiltration technique. Specific and nonspecific bindings were observed in both human serum and HSA. The association constants (K) for the specific bindings were very similar: $1.31 \times 10^5$ $M^{-1}$ in human serum and $3.87 \times 10^5$ $M^{-1}$ in HSA. Glycyrrhizin binds to only the albumin fraction. It was concluded that the glycyrrhizin-binding sites in human serum exist mainly on albumin and glycyrrhizin binds to specific and nonspecific binding sites at lower and higher concentrations than approximately 2 mM, respectively. Ishida S; Sakiya Y; Ichikawa T; Kinoshita M; Awazu S, *Chem Pharm Bull* (Tokyo) 37 (1). 1989. 226–228.

Comparison by equilibrium dialysis of plasma protein binding sites for carbenoxolone in people under 40 yr of age and in people over 65 yr of age showed that the number of binding sites was reduced in the elderly and that this fall was associated with a reduction in plasma albumin levels. Hayes M J; Sprackling M; Langman M, *Gut* 18 (12) 1977 1054–1058.

Albumin has been used as an emulsion stabilizer oil-and-water emulsion injectable medical preparations, e.g. fluorbiprofen, Mizushima et al, U.S. Pat. No. 4,613,505, Sept. 23, 1966; as a binding molecule for tryptophan, Pollack, U.S. Pat. No. 4,650,789, Mar. 17, 1987; with chemical modification as complexing agents for cholesterol derivatives, Arakawa, U.S. Pat. No. 4,442,037, Apr. 10, 1984; as conjugates with enzyme chemically linked to an antibody, Poznansky, U.S. Pat. No. 4,749,570, June 7, 1988; and as chemically coupled conjugates of leukotrienes, Young, et al, U.S. Pat. No. 4,767,745, Aug. 30, 1988.

See UNIQUE FEATURES OF ALBUMIN: A BRIEF REVIEW, Thomas E. Emerson, Jr., Ph.D., *Critical Care Medicine*, Vol. 17, No. 7 (1989), for a recent review of the characteristics of albumin.

The major hazard in producing fractions from large pools of plasma is the transmission of virus, the most serious, being hepatitis. This is a danger both for the recipient of the fractions and for the workers in fractionation plants. It has been shown that fractionation workers, particularly those engaged in the preparation of plasma pools, are at high risk of developing hepatitis B.

Another hazard of plasma fractionation is the partial denaturation of some fractions such as ISG, caused by the fractionation methods. These denatured proteins may have toxic effects or may be immunogenic in the recipients. Among these undesirable side effects is the significant degree of loss of biological competence and the loss or blockage of many binding sites on albumin are lost by the inherent denaturation resulting from this pasteurization or heating process. According to present technology, the disadvantages of denaturation are more than compensated for by the increased stability and potency of concentrated fractions, but there remains a great need for a fully bio-competent albumin.

SUMMARY OF THE INVENTION

It has now been discovered that glycyrrhizin, carbenoxolone and cicloxolone and the analogues thereof inactivate BVD in FCS and other nutrient sera products.

Viral inactivation, as used here, means rendering the virus non-infective, i.e. the virus does not induce disease in a patient. In most instances traditional methods of quantifying virus population growth and reduction, e.g. log kill (See Fraenkel-Conrat, H., Kimball, P. C., and Levy, J. A. VIROLOGY, Second Edition, Prentice Hall, Englewood Cliffs, N.J., 1988, and Jakoby, W. H. and Pastan, I. H. (Eds), CELL CULTURE, (Volume LVIII of "Methods in Enzymology", Academic Press, Inc., New York, Chapter 11) are good indicators of viral inactivation. However, viral inactivation is accomplished by GTPD-Albumin beyond the log kill measurement since any remaining virus are incapable of infecting a patient and are incapable of replicating.

This invention relates to methods for treating FCS and other nutrient sera products, tissue culture media generally, with glycyrrhizic triterpenoid compounds, e.g. glycyrrhizic acid, its analogues such as carbenoxolone and cicloxolone, analogues thereof and the salts, esters and other derivatives thereof, hereinafter referred to as GTPD compounds, and to FCS and other nutrient sera products to inactivate BVD virus.

This invention is embodied in the process of mixing an effective amount of a glycyrrhizic triterpenoid compounds consisting essentially of glycyrrhizin, carbenoxolone, cicloxolone analogues and derivatives thereof, or mixtures thereof with FCS or other nutrient serum or adding the same to tissue culture medium for inactivating BVD.

This invention is also embodied in a composition of matter consisting essentially of FCS or other nutrient serum product containing an amount of one or more glycyrrhizic triterpenoid compounds effective to inactivate BVD.

DESCRIPTION OF THE PREFERRED EMBODIMENTS

According to the present invention FCS and other biologically derived nutrients which may possible contain virus, is treated by adding an effective amount of one or more glycyrrhizic triterpenoid compounds, to a concentration of from about 0.05 to 10 wt/%, typically in the range of from 0.5 to 3 wt/%, to inactivate BVD and CMV and other susceptible viruses.

It has been established that glycyrrhizic triterpenoid compounds in a concentration range of from about 0.005 to 10 wt/%, preferably from about 0.5 to 3 Wt/%, effectively inactivates BVD by at least one log (one logarithmic factor).

Having this discovery to build upon, it is apparent that an effective mode of carrying out the present invention is to provide a mixture of carbenoxolone with either, or both, of glycyrrhizin or cicloxolone, thus obtaining anti-viral.

The GTPD compounds may be used in their acid form, as serum is a very potent buffer; however, it is always necessary to check the pH after adding the GTPD compound and, if necessary, adjust the pH, normally to about 7.0–8.0, e.g. with NaOH or KOH, as certain acid form GTPD compounds drop the pH significantly to the pH 4–5 range.

The acid form of the GTPD compounds is only slightly soluble in water but is quite soluble in dimethyl sulfoxide. The salt, e.g. ammonium, sodium or potassium salts, of the GTPD compounds are, generally, soluble in water, the sodium and potassium salts being more soluble than the ammonium salts. It is, thus, convenient to purchase or prepare the GTPD compounds as sodium or potassium salts.

The preferred method of carrying out the invention comprises mixing with FCS or other nutrient serum or a product comprising the same, or with a tissue culture medium during culturing, an amount of the glycyrrhizic triterpenoid compounds, e.g. glycyrrhizin, carbenoxolone or cicloxolone to comprise from about 0.05 weight/percent to about 10 weight percent of the serum content thereof, such amount being sufficient to inactivate BVD.

If a virus-free tissue culture is once established, it is possible to keep the culture virus-free by adding the glycyrrhizic triterpenoid compounds to comprise from 0.05 to 10 wt/%, normally about 0.5 to 3 wt/%, to each FCS or other serum nutrient, and let the nutrient sit for from 15 minutes to an hour, after careful mixing of the additive serum, to assure inactivation of the serum. The additive serum may then be added to the tissue culture. In such instances, the tissue culture may have a smaller concentration, e.g. 0.001 to 1 wt/%, of glycyrrhizic triterpenoid compounds and yet be virus-free.

It is important to recognize that while the principal discussion has focussed upon FCS because of its technical and economic inportance, this invention is applicable to any serum-containing medium or culture wherein it is desired to assure the absence of BVD, CMV and susceptible viruses and to non-serum media and cultures which may be subject to adventitious viral infection. While serum-based nutrients are a major potential source of infection, the invention is not limited to the inactivation in either such nutrients or in media enriched by such nutrients; rather, the invention is applicable to such nutrients, such media, and to media based upon any source or combination of sources of nutrients.

Data indicate that carenoxolone, over a comparatively short period of time, about an hour or less, is bound by proteins and/or lipids and/or lipoproteins. Such data provide the basis for a nearly ideal method of treatment of media. According to this nearly ideal method, GTPD, e.g. carbenoxolone, is added to a tissue culture medium or nutrient, or the like, which contains or to which lipid, or lipoprotein is added, either contemporaneously or subsequently. The virus in the fluid are inactivated immediately, before the carbenoxolone is completely bound, and, thereafter, the carboxenolone is completely bound. If the lipid or lipoprotein, etc., is added, the addition can be effected after inactivation of the virus.

GTPD-Albumin significantly enhances the effectiveness of the GTPD when added, in lieu of or in addition to GTPD alone, at any stage, directly or indirectly, to the tissue culture medium. An amount of the GTPD compound, e.g. glycyrrhizin, glycyrrhetinic acid, carbenoxolone or cicloxolone in combination with albumin, the combination being referred to as GTPD-Albumin, is added sufficient to inactivate CMV and/or other viruses in the tissue culture medium such that the GTPD comprises from about 0.001 weight/percent (w/%) to about 10 w/%, generally in the range of about 0.05 to about 3 w/%, of tissue culture medium.

Albumin from any source which is safe for intravenous use may be used to form GTPD-Albumin for use in this invention. Conventional caprylate stabilized, heat treated albumin may be used, for example. GTPD-Albumin is prepared simply by mixing GTPD into an albumin solution and allowing the solution to equilibrate a sufficient period of time, a few minutes being sufficient, to assure homogeneity and the formation of GTPD-Albumin. It is convenient to form a saturated solution of GTPD-Albumin, allow it to stand overnight and, if necessary, to filter the solution to assure that any excess GTPD or any precipitate is removed, and then to dilute the GTPD-Albumin solution as desired, or use it full-strength as an additive to tissue culture medium. Prolonged standing or storage, e.g. several days to a few weeks, is not detrimental. The GTPD-Albumin is then mixed with the tissue culture medium and the mixture is maintained at a suitable temperature long enough, as discussed above, to inactivate the virus which may be in the medium. For example, GTPD-Albumin may be prepared the day preceding or a few hours before preparing the medium or adding the GTPD to the medium. The GTPD-Albumin is mixed with the and, preferabbly, the GTPD-Albumin-medium mixture is maintained at about 37° C. plus or minus about 8° C. for an hour or more and the virus-inactivated tissue culture medium may be use in any conventional manner.

Particularly striking results are accomplished using albumin which has not been stabilized in the traditonal way, e.g. with caprylate, and has not been heated. According to the prior art, such an albumin product would be regarded as unsafe because of the potential presence of pathogenic virus. If, however, the stabilization step and the heating step are replaced by the addition of GTPD to the albumin, the virus are inactivated and the albumin is biologically competent. GTPD-Albumin formed in this manner has higher biological activity than GTPD-Albumin prepared from conventional albumin. In a test using a VSV/BVD sensitive cell line performed when the cells were in log phase, the samples were inoculated with $10^9$ pfu of vesicular stomatitis virus (VSV), incubated overnight and serially diluted in MEM with 10% FBS (fatal bovine serum), and then inoculated with VSV. The 0.10% GTPD (carbenoxolone) alone and 0.10% GTPD (carbenoxolone) in 5% solutions of various albumins were introduced at dilutions of from 1:10² to 1:10⁹. The cells were examined daily for five days for virus caused CPE. following table summarizes the comparative results.

| LOG KILL OF VSV BY TPD | |
| --- | --- |
| Albumin Used | Log Kill Five Days |
| None | 4.6 |
| Baxter Buminate ® (U.S. Patent Lot 2746M011AA) | 1.3 |
| Miles Human Albumin Fatty Acid Free (Lot 82-324) | 1.6 |
| Hyland IS 9988 Human Albumin | 2.0 |
| Non-Stabilized, solvent detergent albumin[1] | 5.6+ |

[1]Human serum albumin prepared by Cohn Fractionation, Solvent-Detergent precipitation and alcohol ultrafiltration, not heated and no stabilizer, e.g. caprylate or tryptophan added.

It should be noted that at extreme dilutions of GTPD, binding to albumin may actually reduce antiviral activity; however, higher concentrations of GTPD can be used and the viral inactivation is not decreased even with the least biologically competent albumin and enhancement is generally observed.

Non-stabilized, non-heated albumin is, however, vastly superior to "conventional", i.e. stabilized and pasteurized, albumin, presumably because of a greatly increased ability to form GTPD-Albumin as a result of greater biological competence. Even at extreme dilution, an approximately 6 log kill was found. At lower dilutions (higher concentrations of GTPD) the kill was apparently complete, probably 7 to 9 logs.

It has also been found that the deactivation of antiviral power of GTPD by lipoproteins and/or fatty acids is eliminated or greatly reduced by adding the GTPD as GTPD-Albumin. It is important, therefore, that the GTPD-Albumin be formed using delipidated albumin, to obtain maximum effect with minimum concentration. If, for example, it were desired to add GTPD to tissue culture medium from which lipids and lipoproteins had not been removed, it would be of importance, using the albumin enhancement, to prepare GTPD-Albumin before addition and add the GTPD as GTPD-Albumin. On the other hand, if plasma has been delipidated, GTPD-Albumin can be added directly to the plasma.

The ability of albumin to (a) bind GTPD and (b) not reduce and generally to enhance the viral inactivation power of GTPD. These results mean that GTPD can be carried into the system via albumin without losing its viral inhibition power, can be used at much higher concentrations than would otherwise be possible.

As reported in the prior art, it is known that GTPD will bind to albumin. The nature of the binding, which results in GTPD-Albumin, is not fully understood. GTPD bound to albumin would be expected to be less active chemically and biologically. Quite surprisingly, however, it was found that the viral inactivation characteristics of GTPD bound to albumin were not only not decreased but were, in some instances at least, enhanced.

In all embodiments, the invention exhibits a number of surprising results. The spotty results reported in efforts to determine if, and to what extent, GTPD compounds are indeed virucidal agents led the art to believe, as has been reported, that "the likelihood of developing a blood additive that would kill HIV and HBV and have no effect on laboratory examination of blood seems small." (Peter C. Fuchs, M.L.O., Oct. 1988, 13). In addition, notwithstanding the prior art in which anti-viral activity, to the extent it exists, of GTPD compounds is uncertain, unpredictable and, as yet, unexplained, and the widely accepted proposition that no tissue culture medium additive could be found which would inactivate blood-borne viruses without adversely effecting the tissue culture medium. The present invention embodies a processes and tissue culture medium compositions in which these desired but hitherto unattainable results are accomplished.

Carbenoxolone, alone, at a concentration of 0.01 wt/% was compared with carbenoxolone was compared with 0.01 carbenoxolone containing, respectively, 0.00025, 0.005 and 0.01 wt. % of glycerol, and, in another test, with 0.0005, 0.001 and 0.002 wt. % detergent, TRITON X-100 ®. The test used a VSV/BVD sensitive cell line (EBtr=embryonic bovine tracheal fibroblast). The test was performed when the cells were in log phase to optimize virus-caused CPE. The samples were inoculated with 10⁹ pfu of VSV and incubated. The samples were then serially diluted with MEM with 10% FBS to reach a 9-fold dilution of the virus. The serial dilutions were inoculated in quadruplicate wells (24 well plate of Ebtr cells) and inoculated at 37° C. VSV kill was increased by the addition of glycerol or the detergent, except that extremely dilute solutions of glycerol did not give a significant enhancement of virus inactivation.

Thus, it has been established that an exemplary triterpenoid compound, carbenoxolone, glycyrrhizin and cicloxolone, as well as glycyrrhizic acid and derivatives thereof, typically in the form of salts, in a concentration range of from about 0.001 to 0.005 to 10 wt/% when combined with one or more enhancers, e.g. glycerol, detergent, EDTA or albumin, in the range of from 0.001 to 0.0001 to 5 wt/%, preferably under about 0.001 to 0.01 wt/%, greatly accelerates the inactivation of virus and increases the ultimate inactivation, typically by at least 1 log and as high as 3 logs.

Solutions of glycyrrhizic triterpenoid compounds in the range of from about 0.1 to about 2 or 3 wt/% are presently considered optimal as to concentration, lower concentrations of glycyrrhizic triterpenoid compounds being possible when combined with detergent.

The full scope of types of detergents which may be used in this invention has not been fully determined. The essential requirements are that the detergent have a high detergency action and not interfere with the laboratory tests, at the level of addition involved.

The preferred detergents are classed as nonionic detergents, examples of which include: polyoxyethylene-based detergents such as TWEEN ® and octyl phenoxy polyethoxy ethanol-based detergents such as TriTON X-100 ®, which are preferred, and detergents based upon polyethylene glycol and condensation polymers of ethylene oxide and propylene glycol. These are, of course, merely examples of some of the more common classes of detergents suitable for use in this invention and other classes of nonionic detergents may be used.

Ionic detergents such as, for example, sodium lauryl sulfonates, may also be used, but it may be necessary to make adjustments in the laboratory procedures or results to compensate for the addition of components of the detergent.

A comparison of results using GTPD compounds alone by adding from approximately 0.0001 to 5 wt/%, preferably 0.001 to 1.0 and to 0.0001 to 0.1 wt/% detergent to accomplish virus inactivation, two results were striking. First, inactivation adequate for most purposes, e.g. 2–4 log kills, could be obtained in a fraction of the time previously required. Secondly, the ultimate inactivation was increased by a minimum of 1 log in most cases and typically up to 3 logs, or more, in some instances.

The result was particularly surprising in view of the general lore of the art that low levels of detergent have little or inadequate anti-viral effects. Quite clearly, there is more here than a mere additive effect, since the GTPD effect plus a negligible or zero effect would have been predicted. It is speculated that in some way the detergent renders the cell membrane more accessible to GTPD, which is believed to attach to the membrane but which as no detergency of consequence. This is, however, only a speculation, and there is no hard evidence to support an elucidation of the mechanism of action.

The speed of action and ultimate inactivation achievable using GTPD alone or with detergent is also significantly increased by maintaining the tissue culture medium at approximately body temperature, 27° C. or higher, up to 40°–45° C., preferably, or up to 60° C. if desired to accelerate inactivation or for other reasons.

Unlike the prior art, it is not necessary to remove the very small, trace amounts of non-toxic detergent which is sufficient for the present invention. This feature, alone, is of very significant economic and practical importance.

Solutions of glycyrrhizic triterpenoid compounds in the range of from about 0.01 to about 2 or 3 wt/% are presently considered optimal as to concentration, lower concentrations of glycyrrhizic triterpenoid compounds being possible when combined with glycerol.

A comparison of results using GTPD compounds alone and GTPD modified by adding from approximately 0.0001 to 5 wt/%, preferably 0.001 to 0.1 wt%, glycerol, to accomplish virus inactivation was striking. First, inactivation adequate for most purposes, e.g. 2–4 log kills, could be obtained in a fraction of the time previously required. Secondly, the ultimate inactivation was increased by a minimum of 1 log in most cases and typically up to 3 logs, or more, in some instances.

The result was particularly surprising in view of the general lore of the art that low levels of glycerol have little or inadequate anti-viral effects. Quite clearly, there is more here than a mere additive effect, since the GTPD effect plus a negligible or zero effect would have been predicted. It is speculated that in some way the glycerol renders the cell membrane more accessible to GTPD, which is believed to attach to the membrane but which as no detergency of consequence. This is, however, only a speculation and there is no hard evidence to support an elucidation of the mechanism of action.

Solutions of glycyrrhizic triterpenoid compounds in the range of from about 0.01 to about 2 or 3 wt/% are presently considered optimal as to concentration, lower concentrations of glycyrrhizic triterpenoid compounds being possible when combined with EDTA.

A comparison of results using GTPD compounds alone by adding from approximately 0.001 to 5 wt/%, preferably 0.001 to 1 wt/% EDTA to accomplish virus inactivation was striking. First, inactivation adequate for most purposes, e.g. 2–4 log kills, could be obtained in a fraction of the time previously required. Secondly, the ultimate inactivation was increased by a minimum of 1 log in most cases and typically up to 3 logs, or more, in some instances.

Quite clearly, there is more here than a mere additive effect. It is speculated that in some way the EDTA renders the cell membrane more accessible to GTPD, which is believed to attach to the membrane but which as no detergency of consequence. This is, however, only a speculation and there is no hard evidence to support an elucidation of the mechanism of action.

The present invention is applicable to any process in which cluture media is used, including the manufacture of vaccines.

In the manufacture of vaccines, the GTPD, with or without one or more of the enhancements taught here, is added to a broth, culture or other medium, e.g. egg white protein, etc., which contains the disease-causing virus in an amount sufficient to inactivate the virus. Additions in the range of 0.0001 to 10 wt%, typically from 0.5 to 5 wt%, based on the medium, are sufficient to inactivate the virus. The virus, when used to innoculate the patient, will cause the patient (animal or human) to produce antibodies there by providing an immunity from infection by infectious virus.

The present invention may also be used in the production of biologically or genetically engineered vaccines, drugs and other materials. In such procedures it is frequently necessary to use cell lines as sources of biological constituents and to provide nutrient for these cell lines. The presence of virus in the nutrient or the cell line medium may inhibit or prevent the production of the desired biological product or so contaminate the biological product as to render it useless for therapeutic purposes. GTPD, with or without one or more of the enhancements taught here, is added to a broth, culture or other medium supports the cell line, either before or during the culturing of the cell line, in an amount sufficient to inactivate the virus. Additions in the range of 0.0001 to 10 wt%, typically from 0.5 to 5 wt%, based on the medium, are sufficient to inactivate the virus.

The GTPD compounds can be mixed with other active compounds with synergistic results in inactivation of virus. Such synergistic and potentially synergistic compounds include the anti-viral drug AZT, which is known to act synergistically with the GTPD compounds, dextrans, butyl hydroxy toluene, fatty acids such as oleic acid, chelating agents such as EDTA, and compounds of transition and heavy metals.

Other enhancements and modifications are within the scope of this invention.

INDUSTRIAL APPLICATION

This invention is useful in the manufacture of vaccines, the production of cell lines, and in other applications where biological nutrients are involved.

What is claimed:

1. A method for treating tissue culture medium comprising mixing such tissue culture medium with a composition consisting essentially of one or more glycyrrhizic triterpenoid compounds in a concentration of from about 0.0001 to about 5 wt/% based on culture medium and from about five to about one hundred times that amount of delipidated albumin, the concentration being sufficient to substantially inactivate susceptible viruses found in animal fluids and tissues.

2. The method of claim 1 comprising the further step of maintaining the tissue culture medium at a temperature of from about 37 Deg. C. to about 60 Deg. C. for a period of up to about 24 hours to assure at least a 3-log inactivation of virus in the tissue culture medium.

3. The method of claim 1 comprising mixing said glycyrrhizic triterpenoid compounds with the culture medium in an amount sufficient to form a concentration of from about 0.001 to about 3 wt/% in the tissue culture medium.

4. A composition of matter consisting essentially of tissue culture medium, one or more glycyrrhizic triterpenoid compounds in a concentration of from about 0.0001 to about 5 wt/% based on tissue culture and from about five to about one hundred times that amount of delipidated albumin from a source other than the tissue culture medium, sufficient to substantially inactivate susceptible viruses found in said tissue culture medium.

5. In the process of producing biologically or genetically engineered materials from a cell line in a nutrient medium, the improvement comprising adding to said nutrient medium from about 0.0001 wt/% to about 10 wt/% of one or more glycyrrhizic triterpenoid compounds effective to substantially inactivate susceptible virus said glycyrrhizic triterpenoid compound having been combined with delipidated albumin before addition to said nutrient medium to enhance the viral inactivation.

6. Nutrient for tissue culture medium consisting essentially of serum and a composition consisting essentially of one or more glycyrrhizic triterpenoid compounds in a concentration of from about 0.05 wt/% to about 10 wt/% and delipidated albumin from a source other than the tissue culture medium.

* * * * *